US012642903B2

(12) United States Patent
Kusters

(10) Patent No.: US 12,642,903 B2
(45) Date of Patent: Jun. 2, 2026

(54) ADJUSTMENT OF TARGET INTERFACE POSITION IN A CENTRIFUGE BASED ON LIPID CONCENTRATION

(71) Applicant: Fenwal, Inc., Lake Zurich, IL (US)

(72) Inventor: Benjamin E. Kusters, Pleasant Prairie, WI (US)

(73) Assignee: Fenwal, Inc., Lake Zurich, IL (US)

( * ) Notice: Subject to any disclaimer, the term of this patent is extended or adjusted under 35 U.S.C. 154(b) by 446 days.

(21) Appl. No.: 18/151,597

(22) Filed: Jan. 9, 2023

(65) Prior Publication Data

US 2023/0218814 A1     Jul. 13, 2023

Related U.S. Application Data

(60) Provisional application No. 63/298,468, filed on Jan. 11, 2022.

(51) Int. Cl.
*A61M 1/36* (2006.01)

(52) U.S. Cl.
CPC ... *A61M 1/3693* (2013.01); *A61M 2202/0427* (2013.01)

(58) Field of Classification Search
None
See application file for complete search history.

(56) References Cited

U.S. PATENT DOCUMENTS

| | | |
|---|---|---|
| 6,312,607 B1 | 11/2001 | Brown et al. |
| 2014/0008277 A1 | 1/2014 | Foley et al. |

| | | |
|---|---|---|
| 2014/0231365 A1 | 8/2014 | Cork |
| 2017/0197023 A1 | 7/2017 | Radwanski |
| 2019/0201916 A1 | 7/2019 | Min et al. |

FOREIGN PATENT DOCUMENTS

| | | |
|---|---|---|
| CN | 103635209 A | 3/2014 |
| CN | 107807024 A | 3/2018 |
| WO | 1998043720 A1 | 10/1998 |

OTHER PUBLICATIONS

European Extended Search Report (EESR) from European Patent Application 23150643.7 dated May 22, 2023; 6 pages.
Office Action from related Chinese Patent Application No. 202310027495.6, dated May 31, 2025.

*Primary Examiner* — Krishnan S Menon
(74) *Attorney, Agent, or Firm* — Cook Alex Ltd

(57) ABSTRACT

Systems and methods are provided for improving efficiency and quality of plasma being removed from a blood separation chamber. The system includes a separation chamber in which plasma is separated from cellular blood components, a pump for moving the plasma and an outlet line for removing the separated plasma from the blood separation chamber. An optical sensor assembly is configured to monitor the blood separation chamber and measure an interface position between the separated component and the plasma, and to generate an output indicative of the measured interface position. A controller is programmed to utilize a lipid concentration input of the blood and to set an original lipemia offset, a lipemia threshold and lipemia final setpoint from a predetermined database, and to use a proportional-integral-derivative control loop to assess the actual interface position plus the lipemia threshold to adjust and achieve a final lipemia setpoint for use during separation procedures.

8 Claims, 11 Drawing Sheets

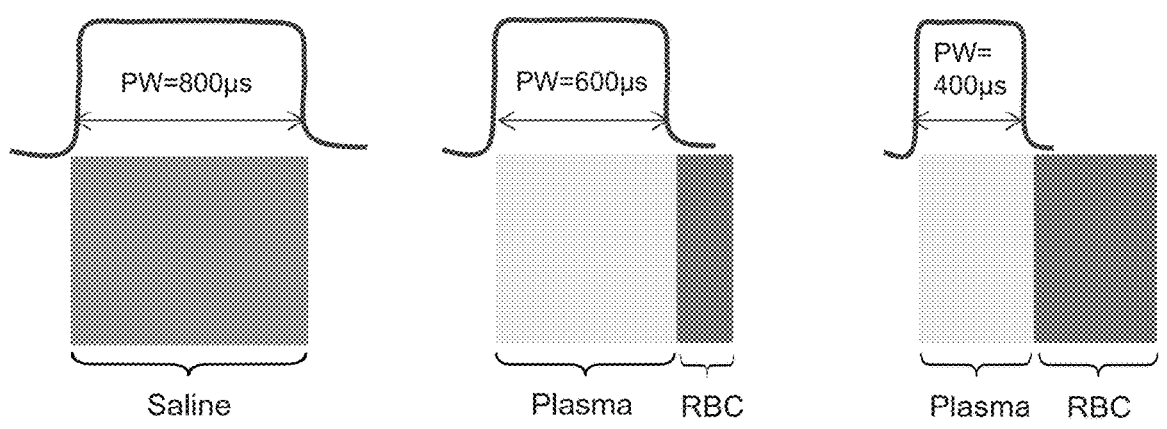
Figure 1
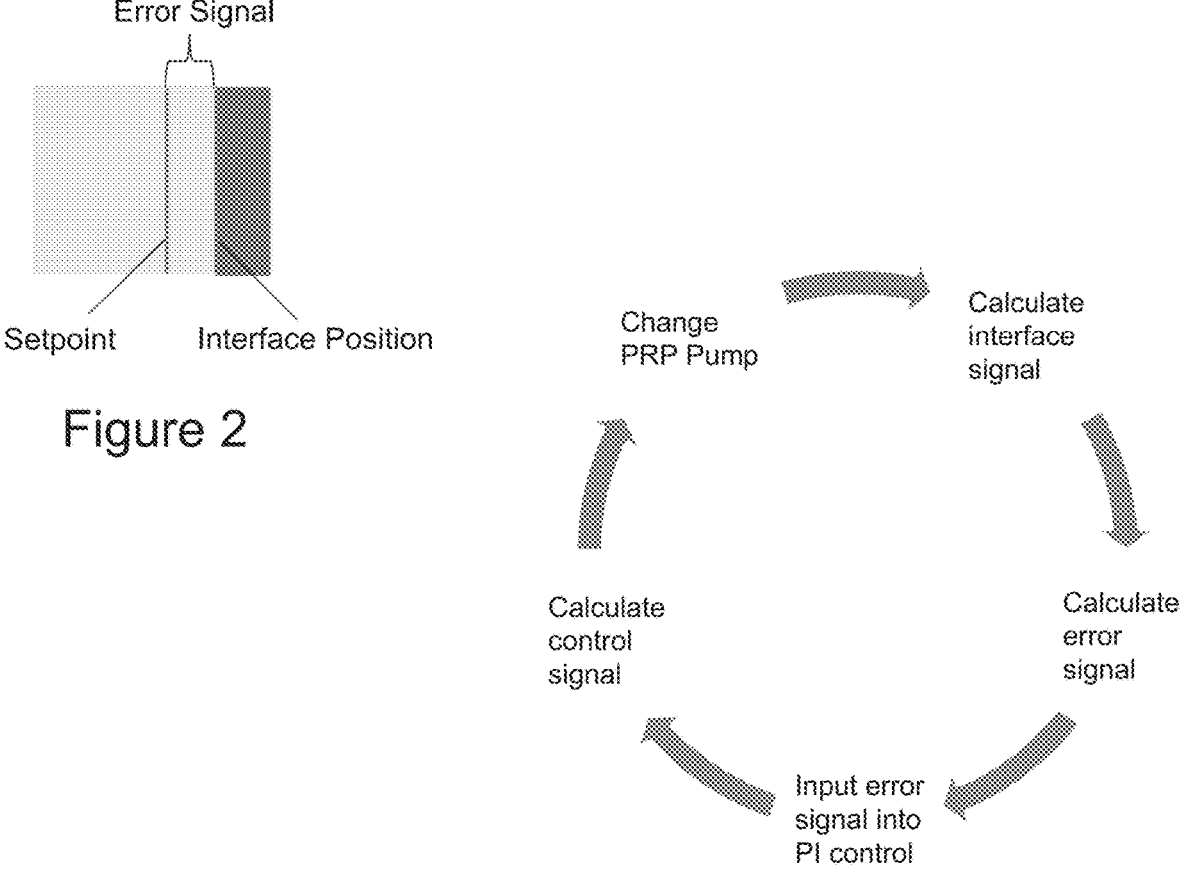
Figure 2
Figure 3

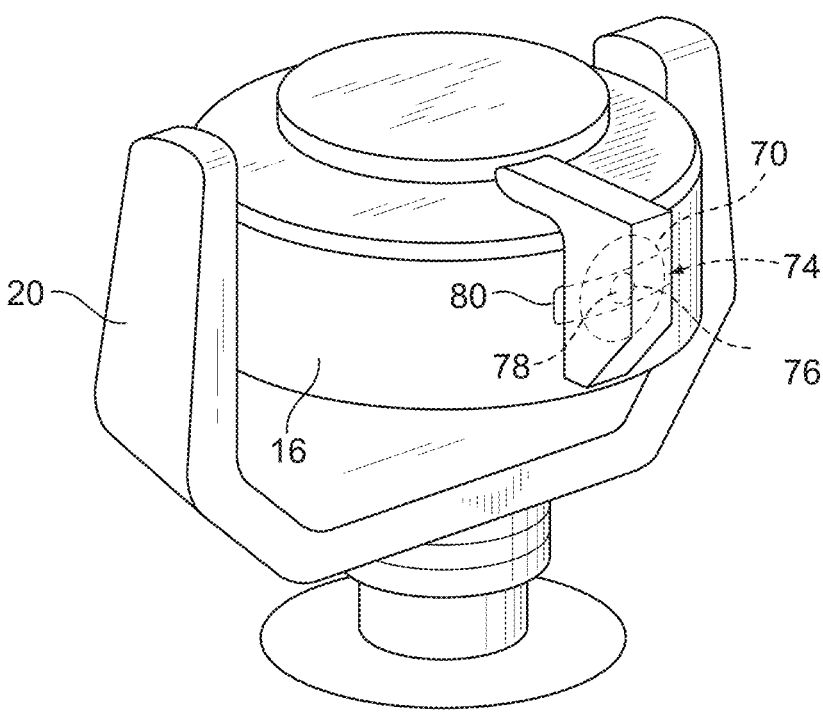
Figure 14
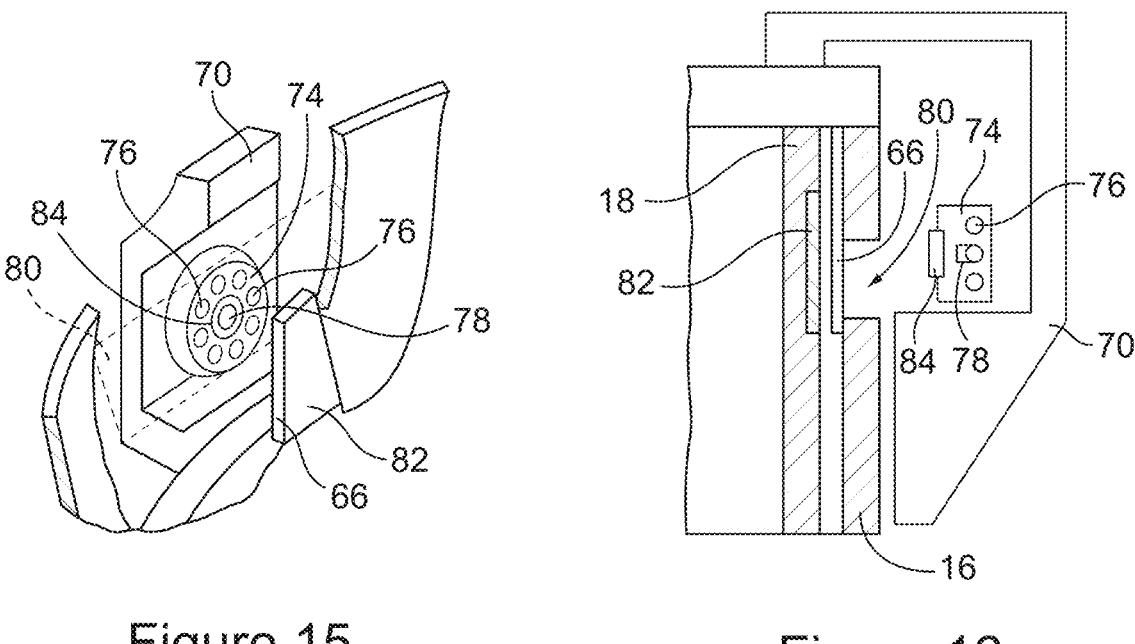
Figure 15          Figure 16

1

ADJUSTMENT OF TARGET INTERFACE POSITION IN A CENTRIFUGE BASED ON LIPID CONCENTRATION

CROSS-REFERENCE TO RELATED APPLICATIONS

This application claims the benefit of and priority to U.S. Provisional Patent Application Ser. No. 63/298,468, filed Jan. 11, 2022, the contents of which are incorporated by reference herein in their entirety.

BACKGROUND OF THE INVENTION

Field of the Disclosure

The present subject matter relates to systems and methods for processing and collecting blood, blood constituents, or other suspensions of cellular material. More particularly, the present subject matter relates to improved blood separation systems and methods employed during blood separation procedures.

Description of Related Art

Various blood processing systems make it possible to collect particular blood constituents, rather than whole blood from a blood source, such as a human donor or patient. Typically, in such systems, whole blood is drawn from a blood source, the particular blood component or constituent is separated, removed and collected, and the remaining blood constituents are returned to the blood source. Removing only particular constituents is advantageous when the blood source is a donor, because potentially less time is needed for the donor's body to return to normal or pre-donation levels. Also, donations of particular blood components or constituents may be made at more frequent intervals than when whole blood is collected. This increases the overall supply of blood constituents, such as plasma and platelets, made available for transfer and/or therapeutic treatment or health care.

Whole blood typically may be separated into its constituents through centrifugation. This requires that the whole blood be passed through a centrifuge after it is withdrawn from, and before it is returned to, the blood source. To reduce contamination and possible infection, if the blood source is a donor or patient, the blood preferably is contained and processed within a disposable, sealed, sterile fluid flow circuit during the entire centrifugation process. Disposable flow circuits include a separation chamber portion, which an operator installs in a durable, reusable centrifuge assembly containing reusable hardware (centrifuge, drive system, pumps, valve actuators, programmable controller, and the like) that rotates the separation chamber and controls the flow through the disposable flow circuit during its use when mounted on and in cooperation with the hardware. The centrifuge assembly engages and rotates the separation chamber in the fluid processing assembly during a collection procedure. The blood, however, makes actual contact only with the fluid processing assembly, which assembly is used only once and then discarded.

Prior to or shortly after loading a disposable circuit into the centrifuge assembly, the operator typically enters, for example, by means of a touch screen or other user interface system, a particular processing protocol to be executed by the system (e.g., a procedure wherein platelets are separated from whole blood and collected) and other parameters (e.g., the weight of the donor, the desired volume of the separated blood component to be collected, etc.). When the system has been programmed, the operator phlebotomizes a donor and the system carries out the procedure, under the supervision of the operator.

As the centrifuge assembly rotates the separation chamber of the disposable flow circuit, the heavier (greater specific gravity) components of the whole blood in the separation chamber, such as red blood cells, move radially outwardly away from the center of rotation toward the outer or "high-G" wall of the separation chamber. The lighter (lower specific gravity) components, such as plasma, migrate toward the inner or "low-G" wall of the separation chamber. Various components can be selectively removed from the whole blood by including appropriately located channeling structures and outlet ports in the separation chamber of the disposable flow circuit. For example, therapeutic plasma exchange involves separating plasma from cellular blood components, collecting the plasma, and returning the cellular blood components and a replacement fluid to the blood source. Alternatively, red blood cells may be harvested from the separation chamber and the rest of the blood constituents returned to the donor. Other processes are also possible including, without limitation, platelet collection, red blood cell exchanges, plasma exchanges, etc.

Proper separation requires, however, that the interface between the separated components be located within a particular zone between the high-G and low-G walls of the separation chamber. For example, when performing a therapeutic plasma exchange procedure, the interface between the plasma and the cellular blood components affects the performance of the system. If the interface is located too close to the low-G wall, then the collected plasma may become unduly populated or contaminated by cellular blood components. On the other hand, if the interface is located too far from the low-G wall, there may be no contamination of the plasma, but the separation efficiency of the system may be decreased with less plasma collected over time.

Various centrifuges, such as those shown and described in U.S. Pat. No. 6,254,784 to Nayak et al., U.S. Pat. No. 6,312,607 to Brown et al. and U.S. Pat. No. 11,465,160 to Min et al. (which are incorporated herein by reference), are operable to automatically keep the interface within a desired zone as the centrifuge operates. Typically, the separation chamber of the fluid processing assembly is loaded between the bowl and spool of a centrifuge. A radially inwardly ramped surface is located on the radially outer wall of the separation channel in the bowl wall of the separation chamber. The interface between the generally dark, opaque red blood cell layer and the generally light, clear plasma layer appears as a line on the ramped surface. Where, exactly, the line appears on the ramped surface is a function of the position of the interface between the high-G and low-G walls of the separation chamber. Accordingly, the position of the line on the ramped surface can be used to gauge the position of the interface between the high-G and low-G walls.

Automatic control over the location of the interface has been achieved by sensing the position of the line on the ramped surface and thereafter adjusting the centrifuge operating parameters to place and keep the line within desired limits. In particular, by controlling the rate at which plasma is withdrawn from the separation chamber, the line can be "moved" up (radially inwardly) or down (radially outwardly) on the ramped surface, such as by decreasing or increasing the plasma flow rate. An optical sensor assembly may be used to sense the position of the line on the ramped surface. Optical control systems commonly operate based on the principle that light will transmit through optically clear fluid, such as saline and plasma (platelet rich plasma, PRP, or plasma poor plasma, PPP), while light will not transmit through optically dense fluid, such as whole blood, WB, or packed Red Blood Cells, RBCs. Thus, when using a light source and detector apparatus, as in the prior systems, optical signals representative of the optical clear fluid thickness within a centrifuge can be measured and applied to calculate and maintain the location of the RBC/plasma interface or interface position.

As the centrifuge spins past the sensor, the sensor develops an electrical pulse having a width related to the position of the line on the ramped surface. As the line moves closer to the high-G wall of the separation chamber, the pulse width increases. As the line moves closer to the low-G wall, the pulse width narrows. By sensing the width of the pulses developed by the optical sensor and thereafter using the pulse width to increase or decrease the rate at which plasma is withdrawn from the separation chamber, the system attempts to keep the line within desired positional limits on the ramped surface and to maintain the interface in the desired radial position or range of positions.

At the start of a separation procedure, saline may be present in the centrifuge during a calibration phase and a light source, such as a laser light, will be transmitted through the entire width of the centrifuge ramp. The signal produced is referred to as the Saline Calibration Signal and represents the width of the entire centrifuge gap without any RBCs present. This signal serves as the reference for calculating the RBC/plasma interface position throughout a procedure. The RBC/plasma interface position is defined as the percentage of the Saline Calibration Signal covered by RBCs. For example, an interface position of 40% signifies that 40% of the original Saline Calibration Signal is blocked by RBCs.

The interface position is indicative of the RBC bed thickness in the centrifuge but is not a literal representation of the RBC bed. That is, an interface position of 40% does necessarily correlate to an RBC bed that takes up 40% of the centrifuge gap between the high-G and low-G walls. FIG. 1 displays an example of signals produced by a photodetector for the saline calibration and increasing RBC bed thickness. The pulse width, PW, of the voltage signal, represented as the measurement threshold by dual sided arrows in FIG. 1, is measured in time and is the key signal characteristic applied in the calculation of the interface position. The PW is a measurement taken at a predetermined voltage threshold, such as 20% of the signal amplitude. FIG. 1 represents cross sections of the fluid gap and the optical signal PW is shown for the saline S calibration (at left, e.g., PW=800 μs) relative to increasing RBC bed thickness, which is represented by the PW for the plasma, such as PRP or PPP, decreasing from (at center, e.g., PW=600 μs to at right PW=400 μs) as RBCs build up in the fluid gap, in turn, decreasing the plasma width through which light can be transmitted.

Thus, the system controller may compare the PW of a measured signal during processing to the PW generated during the saline calibration phase, which corresponds to the pulse width when light is transmitted to the light detector over the entire width of the ramp. Comparing these two PWs will indicate the percentage of the ramp that is occupied by the plasma layer and by the RBC layer, which information the controller may use to determine the location of the interface position INT within the channel. In particular, the interface position may be calculated as follows:

Interface Position (%)=[(Saline Calibration Pulse Width−Current Plasma Pulse Width)/Saline Calibration Pulse Width]×100.

Once the interface position is calculated, it is compared to an ideal, target or targeted position, known as the interface position Setpoint. The difference between the calculated interface position INT and the interface position Setpoint is considered the Error Signal (Error Signal=Setpoint−Interface Position), which represents how far the interface position INT is from where it should ideally be located, as depicted in FIG. 2.

The Error Signal is fed into a proportional integral, PI, or proportional-integral-derivative, PID, based control loop in a controller to calculate the plasma rate required to bring the Interface Position INT closer to the Setpoint, based on how far the Interface Position INT is from the Setpoint (Proportional Term, P), and how long and how far the Interface Position INT has been from Setpoint (Integral Term, I) for a PI controller, and also including the rate of change of the Interface Position (Derivative Term, D) for a PID controller. An example controller control loop is represented in FIG. 3. In general, a slower PRP rate will lower the Interface Position toward the high-G wall, while a faster PRP rate will raise the Interface Position toward the low-G wall.

An existing complication may occur due to the presence of lipids in blood. A condition when lipids are present in high concentrations is known as lipemia. Lipemia will decrease the optical clarity of plasma as lipids remain in plasma fraction during centrifuge separation. In certain example systems offered by Fenwal, Inc. of Lake Zurich, Illinois, which is an affiliate of Fresenius Kabi AG of Bad Homburg, Germany, such as Amicus, and AmiCore (and in future systems such as that described in U.S. Pat. No. 11,465,160 to Min et al., which is incorporated herein by reference), the rising edge of the signal is located on the low-G side of the fluid gap while the falling edge is toward the high-G side. Due to the design of the interface detection "ramp" applied in all three systems, the fluid thickness over which the signal is measured increases from the low-G to high-G sides of the separation chamber. As the concentration of lipids increases and the optical clarity decreases, the light transmission through the plasma layer will decrease, in particular as the fluid thickness increases. Therefore, when lipemic plasma is present, rather than producing a signal with a rather constant amplitude across the signal's width, as previously shown, the signal amplitude is likely to decrease as the fluid thickness increases from the low-G to high-G sides, because less light is transmitting through the continuously thickening fluid layer, such as is shown by the example signal in FIG. 4 and the experimental data shown in FIG. 5.

A signal with a gradual decease in amplitude is likely to cause the falling edge to cross the PW measurement threshold at a location within the plasma fraction rather than at the interface position between the RBC and plasma fractions, as intended. In light of this, the system may calculate the interface position to be at a location higher (artificial interface with larger %) than the actual location of the RBC/plasma interface. Therefore, the system will not measure a significant Error Signal and is likely to maintain an artificial interface position at the target Setpoint, while the actual interface position remains much lower throughout a procedure. Thus, it will be appreciated that the presence of lipids in blood may lead to poorer platelet separation efficiencies than desired in existing systems.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

The apparatus and method of the present disclosure seeks to control the actual interface position at a higher location when lipemic plasma creates poor signals, so as to ensure acceptable collection efficiencies are achieved.

In one aspect, a blood separation system is provided with a blood separation chamber configured to process blood to separate at least one cellular component from plasma. The system includes an input device for providing a lipid concentration within the blood to be processed, a pump for moving the plasma and an outlet line associated with the blood separation chamber for removing at least a portion of the plasma from the blood separation chamber. An optical sensor assembly is configured to directly monitor the interior of the blood separation chamber and to measure an interface position between the separated component and the plasma, and to generate an output indicative of the measured interface position. A controller is programmed to receive the lipid concentration within the blood from the input and to set an original lipemia offset, a lipemia threshold and lipemia final setpoint from a predetermined database, wherein the setpoint equals an ideal interface position that would be required to achieve acceptable separation efficiency of plasma without lipids plus the original lipemia offset, wherein the controller is further programmed with a proportional-integral-derivative control loop to continue to measure the interface position and to assess whether the actual interface position is greater than the ideal interface position plus the lipemia threshold, wherein the controller continues said measuring and assessing until the setpoint equals the final lipemia setpoint.

In another aspect, a method of separating blood is provided which includes receiving an input providing a lipid concentration within blood to be processed and separating at least one cellular component of the blood from plasma in a blood separation chamber. The method further includes monitoring the interior of the blood separation chamber and measuring an interface position between the separated component and the plasma using an optical sensor assembly, generating an output indicative of the measured interface position, and operating a plasma pump to remove at least a portion of the separated plasma from the blood separation chamber. The method further includes setting an original lipemia offset, a lipemia threshold and lipemia final setpoint received from a predetermined database, wherein the setpoint equals an ideal interface position that would be required to achieve acceptable separation efficiency of plasma without lipids plus the original lipemia offset, and utilizing a proportional-integral-derivative control loop to continue measuring the interface position and assessing whether the actual interface position is greater than the ideal interface position plus the lipemia threshold until the setpoint equals the final lipemia setpoint.

In further aspects, the method may include wherein receiving the input providing a lipid concentration within the blood to be processed further comprises accepting a lipid concentration input from an operator input device or from a second optical sensor attached to a platelet poor plasma line from the separation chamber. The method may further include adjusting the setpoint by increasing the setpoint to a higher position than the ideal position, wherein the increase is a lipemia offset defined by the difference between an artificial higher interface position and an actual measured interface position. Moreover, adjusting the setpoint by increasing the setpoint to a higher interface position than the ideal position may generate an error signal that represents the difference between the artificial interface position and the setpoint at the higher interface position. The method further includes setting a flow rate of the plasma pump at which the plasma is removed from the blood separation chamber via an outlet line and such that the error signal causes control logic in a controller to increase the plasma pump flow rate to adjust by increasing the artificial interface position to move toward the increased setpoint, which in turn adjusts by increasing the actual interface position toward the higher ideal interface position. Upon the increase in the plasma flow rate the method further includes monitoring an increase in the actual interface position, monitoring the artificial interface position, a decrease in the lipemia offset, the error signal as measured between the setpoint and artificial interface position, and wherein the proportional-integral-derivative control loop of the controller continues to output a higher plasma rate which continues to pull the at least one cellular component layer higher.

In still further aspects, the method includes monitoring the actual interface position such that once the actual interface position reaches or surpasses the value of the original ideal interface position by a predetermined threshold dependent upon the lipemia concentration, an adjustment is made to a new final interface set point that is set to a higher location than the original ideal setpoint position to ensure an artificial interface position is not created again later in the separation process. The method also may include repeating the procedure as the lipemia levels decrease overtime while collection is in process due to replenishment of lipid-free fluids to a blood source that compensate for removal of volumes from the blood source.

BRIEF DESCRIPTION OF DRAWINGS

FIG. 1 is a series of schematic diagrams of example optical signal pulse width measurements at cross sections of a fluid gap representing saline, and decreasing pulse width as RBC builds up in the fluid gap thus decreasing the plasma width through which light can be transmitted;

FIG. 2 is a schematic diagram of an example error signal shown as being equal to the Setpoint—Interface Position;

FIG. 3 is a diagram of a control loop of a system controller that seeks to calculate a control signal to change the PRP pump, to then calculate the interface signal in an effort to set the Setpoint to a higher value, which is followed by calculation of an Error Signal and then inputting the Error Signal into the controller to continue to revise the processing toward a higher ideal interface position;

FIG. 14 is a side perspective view of the bowl and spool of the centrifuge when in the operating position, showing a viewing head, which forms a part of the interface controller, being carried by the centrifuge to view the interface ramp during rotation of the bowl;

FIG. 15 is a perspective view of the viewing head, with portions broken away and in section, showing the light source and light detector, which are carried by the viewing head, in alignment with the interface ramp, as viewed from within the spool and bowl of the centrifuge;

FIG. 16 is a side section view of the bowl, spool, and viewing head when the viewing head is aligned with the interface ramp;

DETAILED DESCRIPTION

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 4:
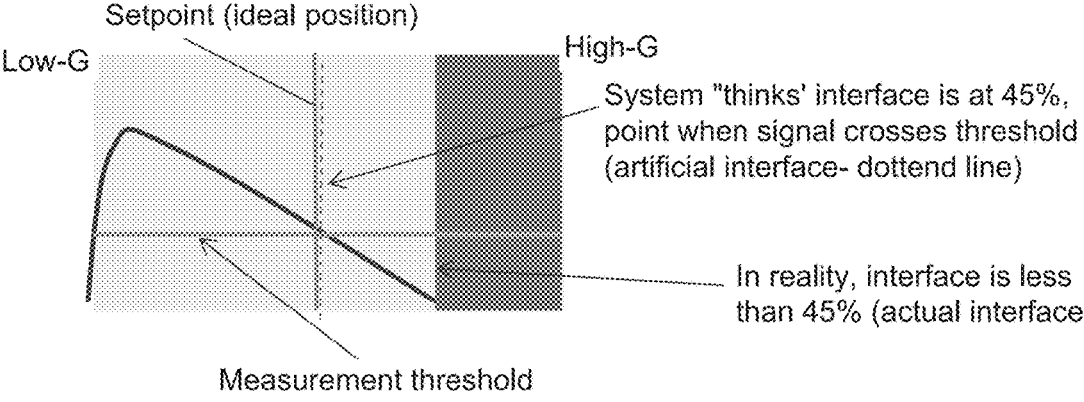
FIG. 4 is a schematic diagram showing an example of the typical impact of lipids in the blood being processed.
Figure 5:
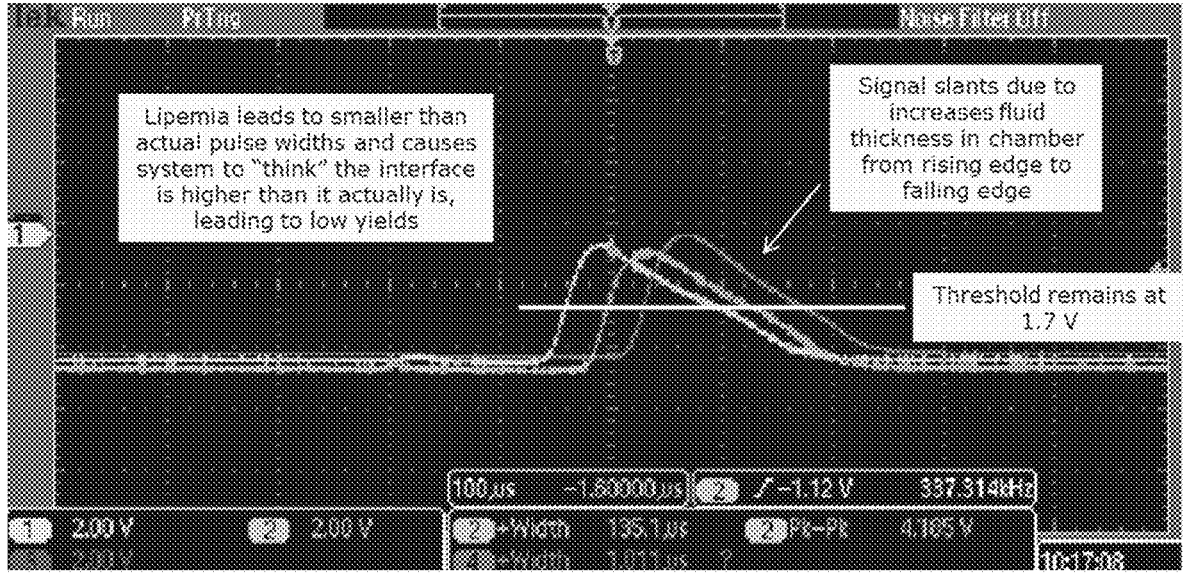
FIG. 5 is an image of experimental data of an optical signal when lipemic plasma is present in the separation chamber.
Figure 6:
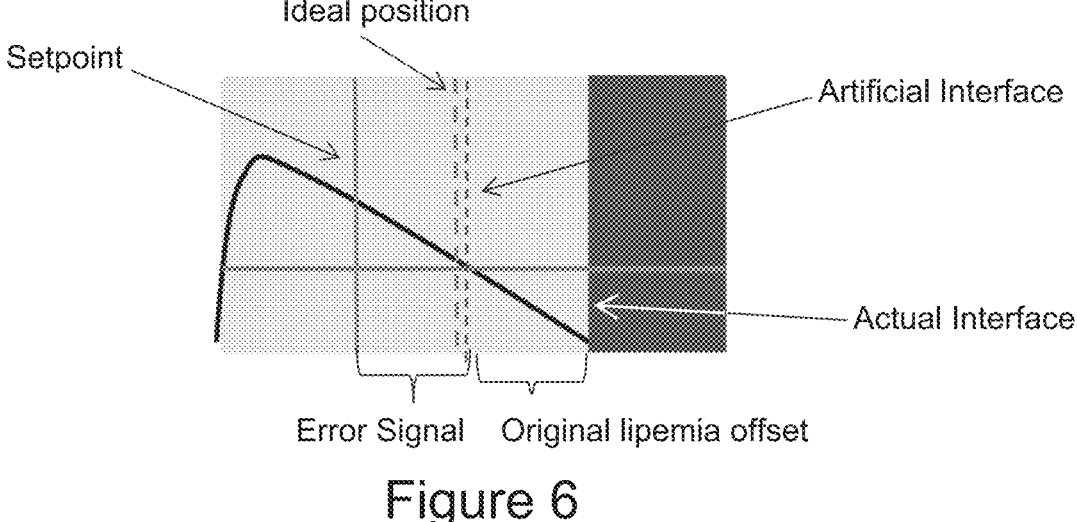
FIG. 6 is a schematic diagram showing an example of an optical signal when lipemic plasma is present in a typical separation chamber.
Figure 7:
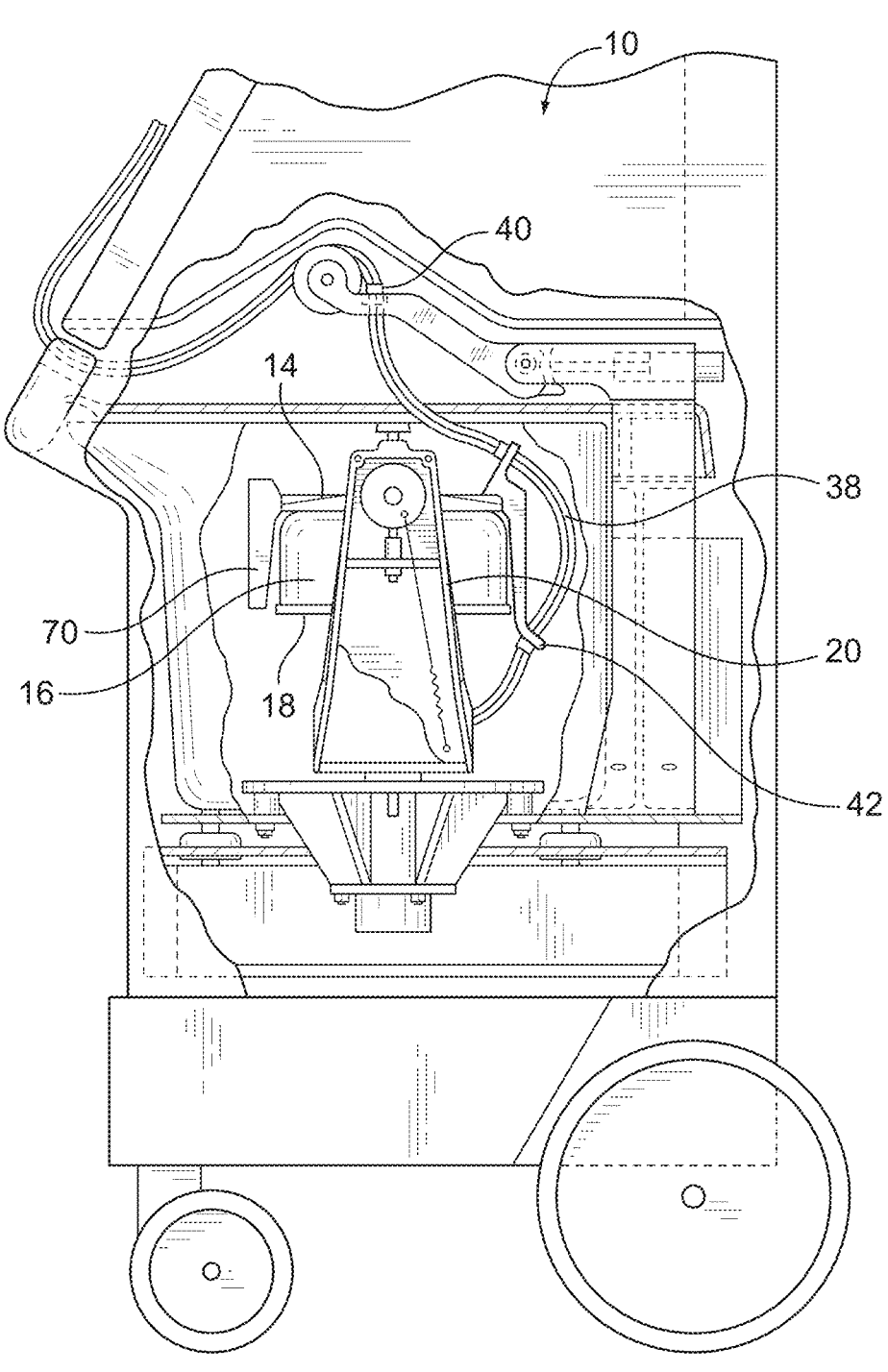
FIG. 7 is a side elevation view, with portions broken away and in section, of a blood separation system employing aspects of the present disclosure, with a centrifuge bowl and spool of the system being shown in their operating position.
Figure 8:
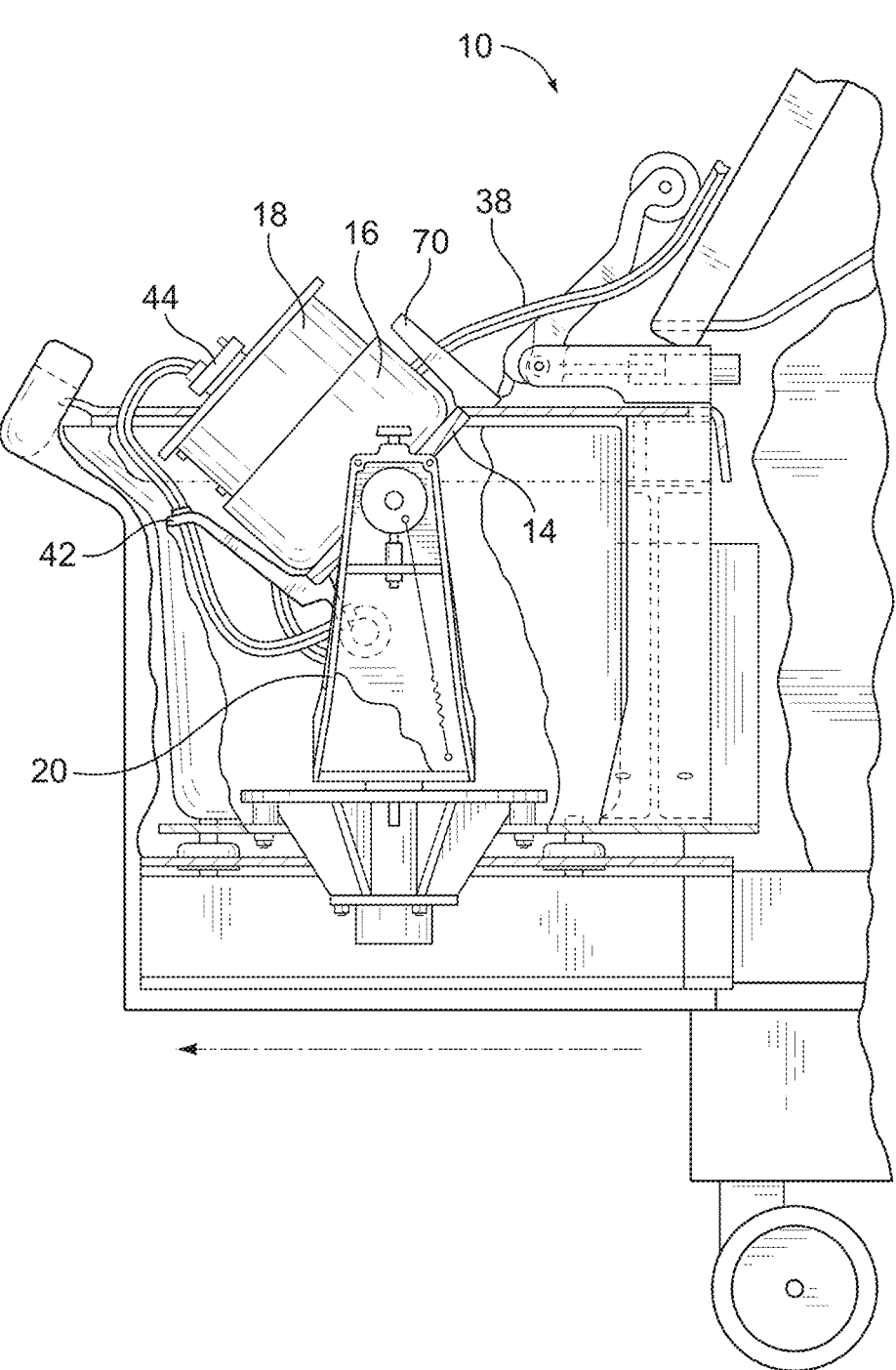
FIG. 8 is a side elevation view, with portions broken away and in section, of the system shown in FIG. 7, with the bowl and spool shown in an upright position for receiving a blood separation chamber.

The method of the present disclosure is described herein in the context of an example apparatus. FIGS. 7 and 8 show a centrifugal fluid processing system 10 with an interface controller 12 (FIG. 17) that may be used in practicing the interface control principles of the present disclosure. The system is shown with respect to a revised version of the AMICUS® separator marketed by Fenwal, Inc. of Lake Zurich, Illinois, as described in greater detail in U.S. Pat. No. 5,868,696, which is hereby incorporated herein by reference. The system 10 can be used for processing various fluids, but is particularly well suited for processing whole blood, blood components, or other suspensions of biological cellular materials. While interface control principles will be described herein with reference to one particular system 10, it should be understood that these principles may be employed with other fluid processing systems employing different interface control systems without departing from the scope of the present disclosure.

Turning to discussion of the hardware and disposable flow circuit, the system 10 includes a centrifuge 14 used to centrifugally separate blood components. The system 10 may be programmed to separate blood into a variety of components (e.g., PRP and RBC). For illustrative purposes, a therapeutic plasma exchange procedure, in which the centrifuge 14 separates WB into cellular components (e.g., RBCs and platelets) and substantially cell-free plasma, will be described herein. However, the principles described and claimed herein may be employed with other blood separation procedures without departing from the scope of the present disclosure.

The illustrated centrifuge 14 is of the type shown in U.S. Pat. No. 5,316,667 to Brown et al., which is incorporated herein by reference. The centrifuge comprises a bowl 16 and a spool 18. The bowl 16 and spool 18 are pivoted on a yoke 20 between an operating position shown in FIG. 7 and a loading/unloading position shown in FIG. 8.

When in the loading/unloading position, the spool 18 can be opened by movement at least partially out of the bowl 16, as shown in FIG. 8. In this position, the operator wraps a flexible blood separation chamber 22 (see FIG. 9) of a disposable flow circuit about the spool 18. Closure of the spool 18 and bowl 16 encloses the chamber 22 for processing. When closed, the spool 18 and bowl 16 are pivoted to the operating position of FIG. 7 for rotation about an axis.

Figure 10:
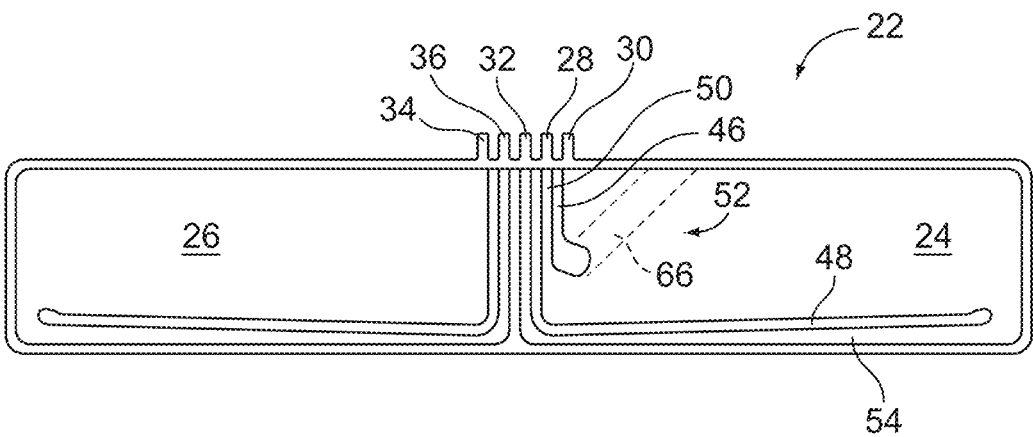
FIG. 10 is a plan view of the blood separation chamber shown in FIG. 9, out of association with the spool.

The blood separation chamber 22 can be variously constructed. FIG. 10 shows a representative embodiment. The chamber 22 shown in FIG. 10 allows for either single or multi-stage processing. When used for multi-stage processing, a first stage 24 separates whole blood into first and second components. Depending on the nature of the separation procedure, one of the components may be transferred into a second stage 26 for further processing.

Figure 9:
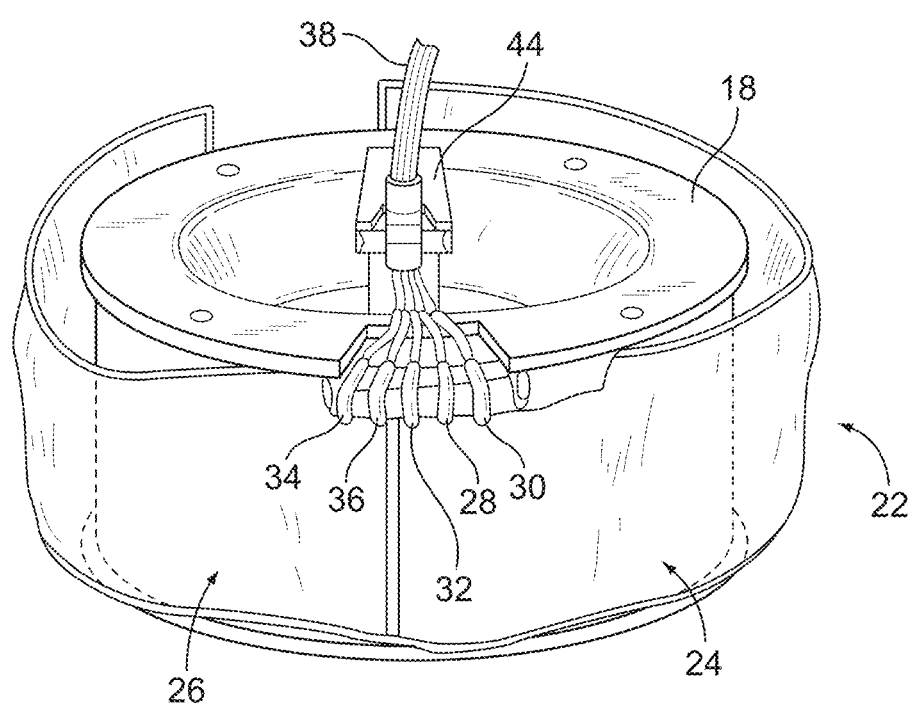
FIG. 9 is a top perspective view of the spool of the centrifuge shown in FIG. 8 in its upright position and carrying the blood separation chamber.

As FIGS. 9 and 10 best show, there are three ports 28, 30, and 32 associated with the first stage 24. Depending on the particular blood processing procedure, the ports may have different functionality but, in a therapeutic plasma exchange procedure, the port identified at 32 is used for conveying blood from a blood source or patient into the first stage 24. During such a therapeutic plasma exchange procedure, the other two ports 28 and 30 serve as outlet ports for separated blood components exiting the first stage 24. More particularly, the first outlet port 30 conveys a low density blood component from the first stage 24, while the second outlet port 28 conveys a high density blood component from the first stage 24.

In a method of carrying out single-stage processing, one of the separated components is returned to the donor, while the other is removed from the first stage 24 and stored. For example, when carrying out a therapeutic plasma exchange procedure, WB in the first stage 24 is separated into cellular components (i.e., a high density component) and substantially cell-free plasma (i.e., a low density component). The plasma is removed from the first stage 24 via the first outlet port 30 for collection and storage, while the cellular components are removed from the first stage 24 via the second outlet port 28 and returned to the donor or patient. Alternatively, rather than collecting and storing the plasma, it may instead be discarded after separation or treated by a secondary device (e.g., an adsorption column) and returned to the donor or patient.

If multi-stage processing is required, one of the components will be transferred from the first stage 24 to the second stage 26 via a port 34 associated with the second stage 26.

The component transferred to the second stage 26 is further fractionated into sub-components, with one of the sub-components being removed from the second stage 26 via an outlet port 36 and the other sub-component remaining in the second stage 26. In the illustrated embodiment, the ports 28, 30, 32, 34, and 36 are arranged side-by-side along the top transverse edge of the chamber 22.

While the same ports 28, 30, and 32 of the first stage 24 are used as in the above-described therapeutic plasma exchange procedure, the ports 28 and 32 have different functionality in a multi-stage separation procedure. In one method of multi-stage operation, blood enters the first stage 24 via the port 28 and is separated into red blood cells, RBCs, (i.e., the high density blood component), and platelet-rich plasma, PRP, (i.e., the low density blood component). The RBCs are returned to the donor (via the port 32), while the PRP is conveyed out of the first stage 24 (via the first outlet port 30) and into the second stage 26 (via the inlet port 34). In the second stage 26, the PRP is separated into platelet-poor plasma, PPP, and platelet concentrate. The PPP is removed from the second stage 26 (via the outlet port 36), leaving platelet concentrate in the second stage 26 for resuspension and transfer to one or more storage containers.

As best shown in FIG. 9, a tubing umbilicus 38 is attached to the ports 28, 30, 32, 34, and 36. The umbilicus 38 interconnects the first and second stages 24 and 26 with each other and with pumps and other stationary components located outside the rotating components of the centrifuge 14 (not shown). As shown in FIG. 7, a non-rotating (zero omega) holder 40 holds the upper portion of the umbilicus 38 in a non-rotating position above the spool 18 and bowl 16. A holder 42 on the yoke 20 rotates the mid-portion of the umbilicus 38 at a first (one omega) speed about the suspended spool 18 and bowl 16. Another holder 44 (FIGS. 8 and 9) rotates the lower end of the umbilicus 38 at a second speed twice the one omega speed (the two omega speed), at which speed the spool 18 and bowl 16 also rotate. This known relative rotation of the umbilicus 38 keeps it untwisted, in this way avoiding the need for rotating seals.

As FIG. 10 shows, a first interior seal 46 is located between the low density outlet port 30 and the high density outlet port 28. A second interior seal 48 is located between the high density outlet port 28 and the blood inlet port 32. The interior seals 46 and 48 form a fluid passage 50 (an outlet for high density blood components in a therapeutic plasma exchange procedure) and a low density collection region 52 in the first stage 24. The second seal 48 also forms a fluid passage 54 (a blood inlet in a therapeutic plasma exchange procedure) in the first stage 24.

Figure 11:
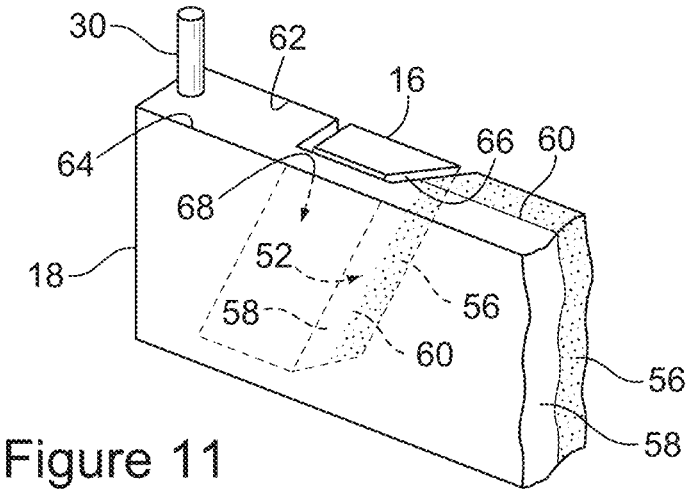
FIG. 11 is an enlarged perspective view of an interface ramp carried by the centrifuge in association with the blood separation chamber, showing the centrifugally separated red blood cell layer, plasma layer, and interface within the chamber when in a desired location on the ramp.

In a therapeutic plasma exchange procedure, the fluid passage 54 channels blood directly into the circumferential flow path immediately next to the low density collection region 52. As shown in FIG. 11, the blood separates into an optically dense layer 56 containing cellular components, which forms as cellular components move under the influence of centrifugal force toward the high-G (outer) wall 62. The optically dense layer 56 will include RBCs (and, hence, will be referred to herein as the "RBC layer") but, depending on the speed at which the centrifuge 14 is rotated, other cellular components (e.g., larger white blood cells and platelets) also may be present in the RBC layer 56.

The movement of the component(s) of the RBC layer 56 displaces less dense blood components radially toward the low-G (inner) wall 64, forming a second, less optically dense layer 58. The less optically dense layer 58 includes plasma (and, hence, will be referred to herein as the "plasma layer") but, depending on the speed at which the centrifuge

14 is rotated and the length of time that the blood is resident in the centrifuge, other components (e.g., platelets and smaller white blood cells) also may be present in the plasma layer 58.

As discussed previously, the transition between the formed cellular blood components and the liquid plasma component is generally shown as a line and referred to as the interface 60 (FIG. 11). Platelets and white blood cells (which have a density greater than plasma and usually less than RBCs) typically occupy this transition region, although that also varies with centrifuge speed and residence time, as is well known in the technical field.

Figure 12:
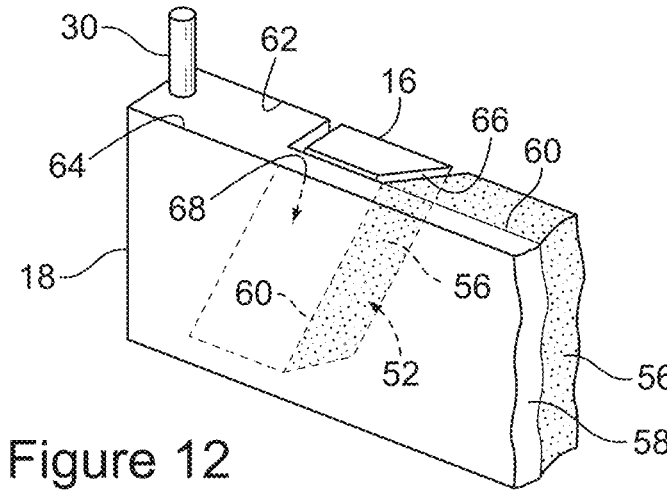
FIG. 12 is an enlarged perspective view of the interface ramp shown in FIG. 11, showing the red blood cell layer and interface at an undesired high location on the ramp.
Figure 13:
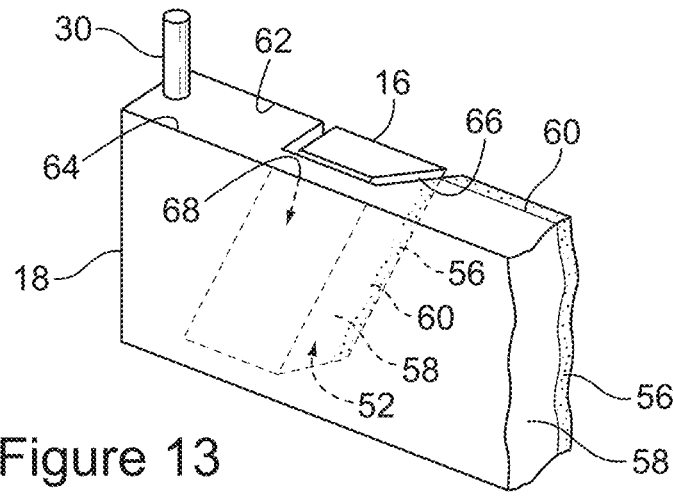
FIG. 13 is an enlarged perspective view of the interface ramp shown in FIG. 11, showing the red blood cell layer and interface at an undesired low location on the ramp.

The location of the interface 60 within the chamber 22 can dynamically shift during blood processing, as FIGS. 12 and 13 show. If the location of the interface 60 is too high (that is, if it is too close to the low-G wall 64 and the removal port 30, as FIG. 12 shows), cellular components can spill over and into the low density collection region 52, adversely affecting the quality of the low density components (typically plasma). On the other hand, if the location of the interface 60 is too low (that is, if it resides too far away from the low-G wall 64, as FIG. 13 shows), the collection efficiency of the system 10 may be impaired.

As FIG. 11 shows, a ramp 66 extends from the high-G wall 62 of the bowl 16 at an angle across the low density collection region 52. The angle, measured with respect to the axis of the first outlet port 30 is about 30° in one embodiment. FIG. 11 shows the orientation of the ramp 66 when viewed from the low-G wall 64 of the spool 18. FIG. 10 shows, in phantom lines, the orientation of the ramp 66 when viewed from the high-G wall 62 of the bowl 16.

Further details of the angled relationship of the ramp 66 and the first outlet port 30 can be found in U.S. Pat. No. 5,632,893 to Brown et al., which is incorporated herein by reference.

The ramp 66 forms a tapered wedge that restricts the flow of fluid toward the first outlet port 30. The top edge of the ramp 66 extends to form a constricted passage or fluid gap 68 along the low-G wall 64. The plasma layer 58 must flow through the constricted passage 68 to reach the first outlet port 30.

As FIG. 11 shows, the ramp 66 makes the interface 60 between the RBC layer 56 and the plasma layer 58 more discernible for detection, displaying the RBC layer 56, plasma layer 58, and interface 60 for viewing through the high-G wall 62 of the chamber 22.

Further details of the separation chamber 22 and its operation may be found in U.S. Pat. No. 5,316,667, which is incorporated herein by reference.

The interface controller 12 (FIG. 17) includes a viewing head or first optical sensor assembly 70 carried on the yoke 20 (see FIGS. 14 and 15). The first optical sensor assembly 70 is oriented to optically view the transition in optical density between the RBC layer 56 and the plasma layer 58 on the ramp 66.

The interface controller 12 is functional to determine the location of the interface 60 on the ramp 66 and, if the interface 60 is located at an improper location (e.g., in the locations of FIG. 12 or 13), to seek to correct the location of the interface 60.

Referring to FIGS. 14-16, the first optical sensor assembly 70, carried by the yoke 20, includes a light source 74, which emits light that is absorbed by red blood cells. In the illustrated embodiment, the light source 74 includes a circular array of red light emitting diodes 76, but other wavelengths absorbed by red blood cells, like green or infrared, also could be used.

In the illustrated embodiment, seven light emitting diodes 76 comprise the light source 74. More or fewer diodes 76 may be used, depending upon the optical characteristics desired. Further, non-LED lights also may be employed without departing from the scope of the present disclosure.

The first optical sensor assembly 70 also includes a light detector 78 (FIGS. 15 and 16), which is mounted adjacent to the light source 74. In one embodiment, the light detector 78 comprises a PIN diode detector, which is located generally in the geometric center of the circular array of light emitting diodes 76. Other types of light detectors also may be employed.

The yoke 20 and the first optical sensor assembly 70 rotate at a one omega speed, as the spool 18 and bowl 16 rotate at a two omega speed. The light source 74 directs light onto the rotating bowl 16. In the illustrated embodiment, the bowl 16 is transparent to the light emitted by the source 74 only in the region 80 where the bowl 16 overlies the interface ramp 66 (FIG. 14). In the illustrated embodiment, the region 80 comprises a window cut out in the bowl 16. The remainder of the bowl 16 that lies in the path of the first optical sensor assembly 70 comprises an opaque or light absorbing material.

The interface ramp 66 is made of a light transmissive material. The light from the source 74 will thereby pass through the transparent region 80 of the bowl 16 and the ramp 66 every time the rotating bowl 16 and first optical sensor assembly 70 align. The spool 18 also may carry a light reflective material 82 (FIGS. 15 and 16) behind the interface ramp 66 to enhance its reflective properties. The spool 18 reflects incoming light received from the source 74 out through the transparent region 80 of the bowl 16, where it is sensed by the detector 78. In the illustrated embodiment, light passing outward from the source 74 and inward toward the detector 78 passes through a focusing lens 84 (shown in FIGS. 15 and 16), which forms a part of the viewing head 70.

Such an arrangement optically differentiates the reflective properties of the interface ramp 66 from the remainder of the bowl 16. This objective can be achieved in other ways. For example, the light source 74 could be gated on and off with the arrival and passage of the ramp 66 relative to its line of sight. As another example, the bowl 16 outside the transparent region 80 could carry a material that reflects light, but at a different intensity than the reflective material 82 behind the interface ramp 66.

As the transparent interface region 80 of the bowl 16 comes into alignment with the first optical sensor assembly 70, the detector 78 will first sense light reflected through the plasma layer 58 on the ramp 66. Eventually, the RBC layer 56 adjacent the interface 60 on the ramp 66 will enter the optical path of the first optical sensor assembly 70. The RBC layer 56 absorbs light from the source 74 and thereby reduces the previously sensed intensity of the reflected light. The intensity of the reflected light sensed by the detector 78 represents the amount of light from the source 74 that is not absorbed by the RBC layer 56 adjacent to the interface 60. With this information, a processing element or module 86 (FIG. 17) can determine the location of the interface 60 on the ramp 66 relative to the constricted passage or fluid gap 68. A more detailed discussion of the algorithms by which the interface controller 12 receives and processes signals to determine the location of the interface 60 on the ramp 66 may be found in U.S. Pat. No. 6,312,607 to Brown et al., which is incorporated herein by reference.

Figure 17:
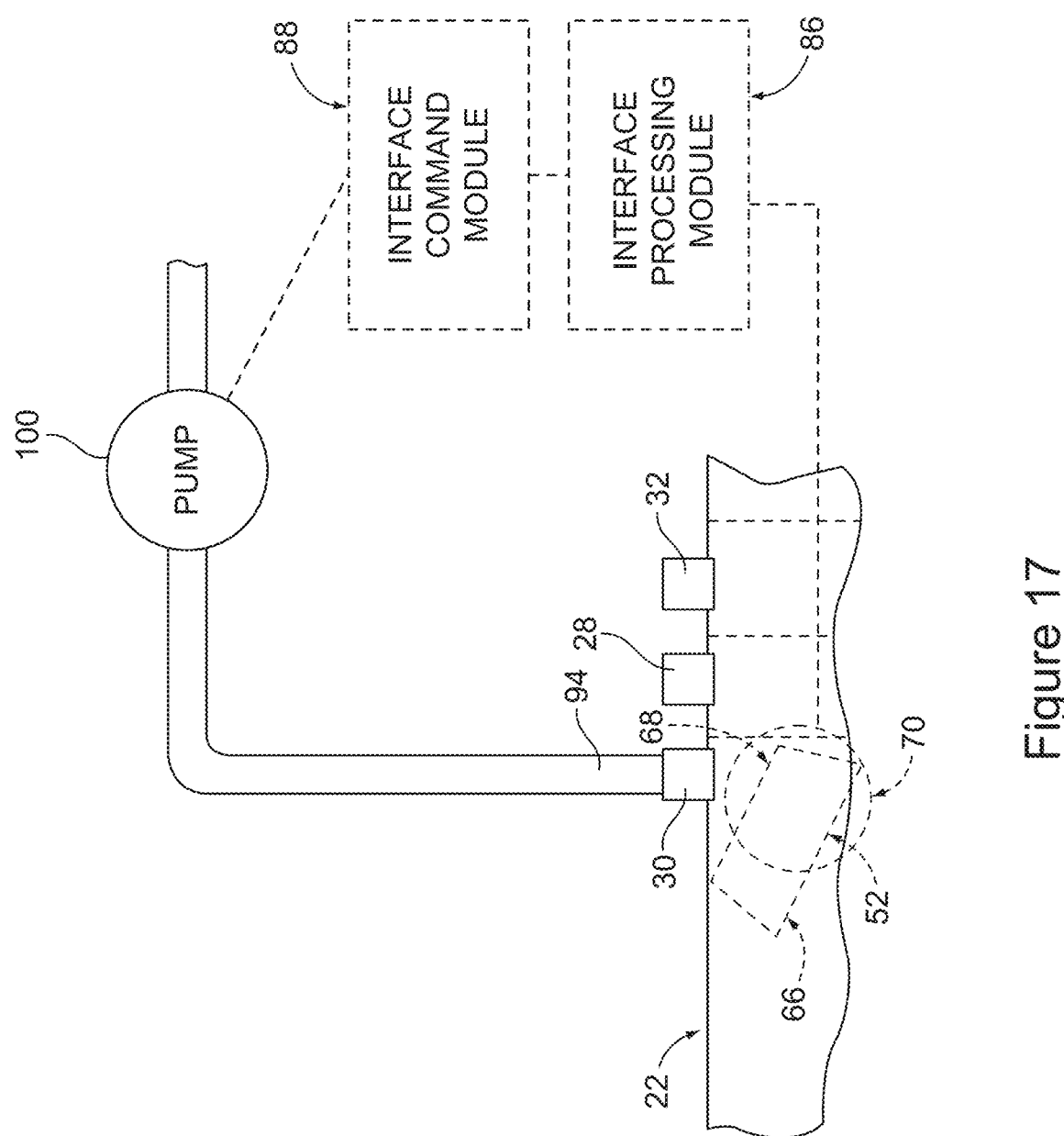
FIG. 17 is a schematic view of a blood calibration element, which forms a part of the interface controller.

When the location of the interface 60 on the ramp 66 has been determined, the processing element 86 outputs that information to an interface command element or module 88 (FIG. 17). The command element 88 includes the logic of the flow diagram in FIG. 3, which calculates the interface position to generate an error signal.

When the control value is expressed in terms of a targeted red blood cell percentage value, a positive error signal indicates that the RBC layer 56 on the ramp 66 is too large (as FIG. 12 shows). The interface command element 88 uses the control logic of FIG. 3 to generate a signal to adjust an operational parameter accordingly, such as by reducing the rate at which plasma is removed through the first outlet port 30 under action of a pump 100 (FIG. 17). The interface 60 moves away from the constricted passage or fluid gap 68 toward the desired control position (as FIG. 11 shows), where the error signal is zero.

A negative error signal indicates that the RBC layer 56 on the ramp 66 is too small (as FIG. 13 shows). The interface command element 88 generates a signal to adjust an operational parameter accordingly, such as by increasing the rate at which plasma is removed through the first outlet port 30. The interface 60 moves toward the constricted passage 68 to the desired control position (FIG. 11), where the error signal is again zero.

Figure 18:
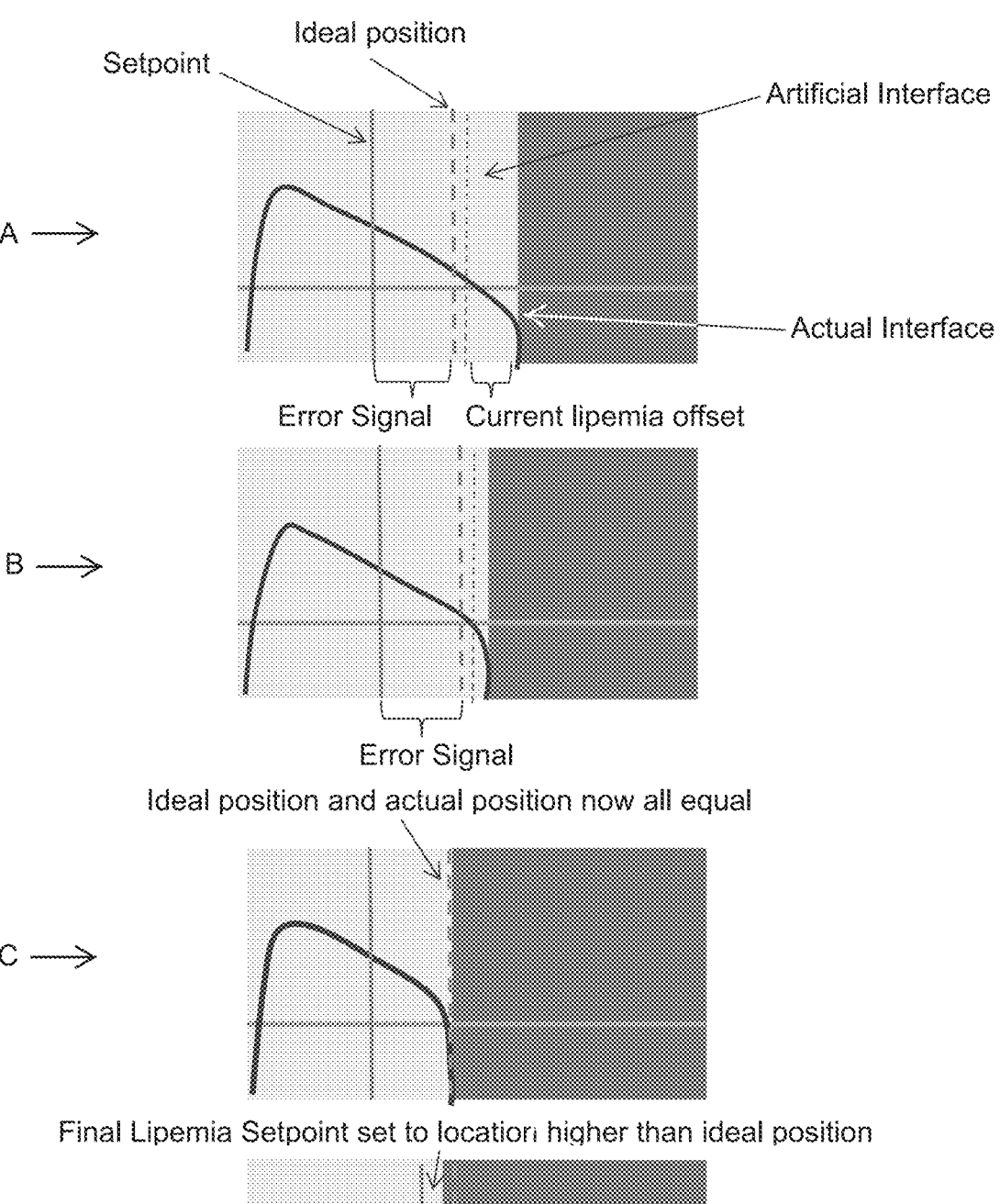
FIG. 18 shows a progression for moving the actual interface.

During normal operation with clean plasma, the optical sensor will generate a pulse width, PW, signal based on the light transmitted through the fluid in the fluid gap. In such instance, as shown at A, the target Setpoint of the control logic represents the ideal interface position required to achieve an acceptable separation efficiency, as seen in FIG. 18. However, as further shown in FIG. 18 at C relative to B, when lipemic plasma leads to a poor optical signal, the target Setpoint of the control logic must be adjusted so as to be set to a higher position to enable the actual interface to reach a higher position that will enable platelet separation. Thus, the Setpoint of the control logic and the ideal interface position may no longer be equal, in particular when the system is originally increasing the RBC layer 56 thickness to the ideal position at the start of a procedure as the thickness of the plasma layer 58 will be at maximum allowing the falling edge of the signal to be impacted by the lipemic plasma.

Instead, the Setpoint may be adjusted by increasing it to a higher location than the ideal position, such as equal to the difference between the artificial interface and the actual interface shown in FIG. 18 at B, which will be referred to as the lipemia offset. Adjusting to set the Setpoint to a higher value creates an Error Signal between the artificial interface position and the Setpoint, thus causing the PID control loop logic in FIG. 3 above to increase the plasma pump flow rate in an attempt to adjust and increase the artificial interface position towards the Setpoint, which in turn will increase the actual interface position towards the higher ideal position, as shown in FIG. 18 at C.

Figure 19:
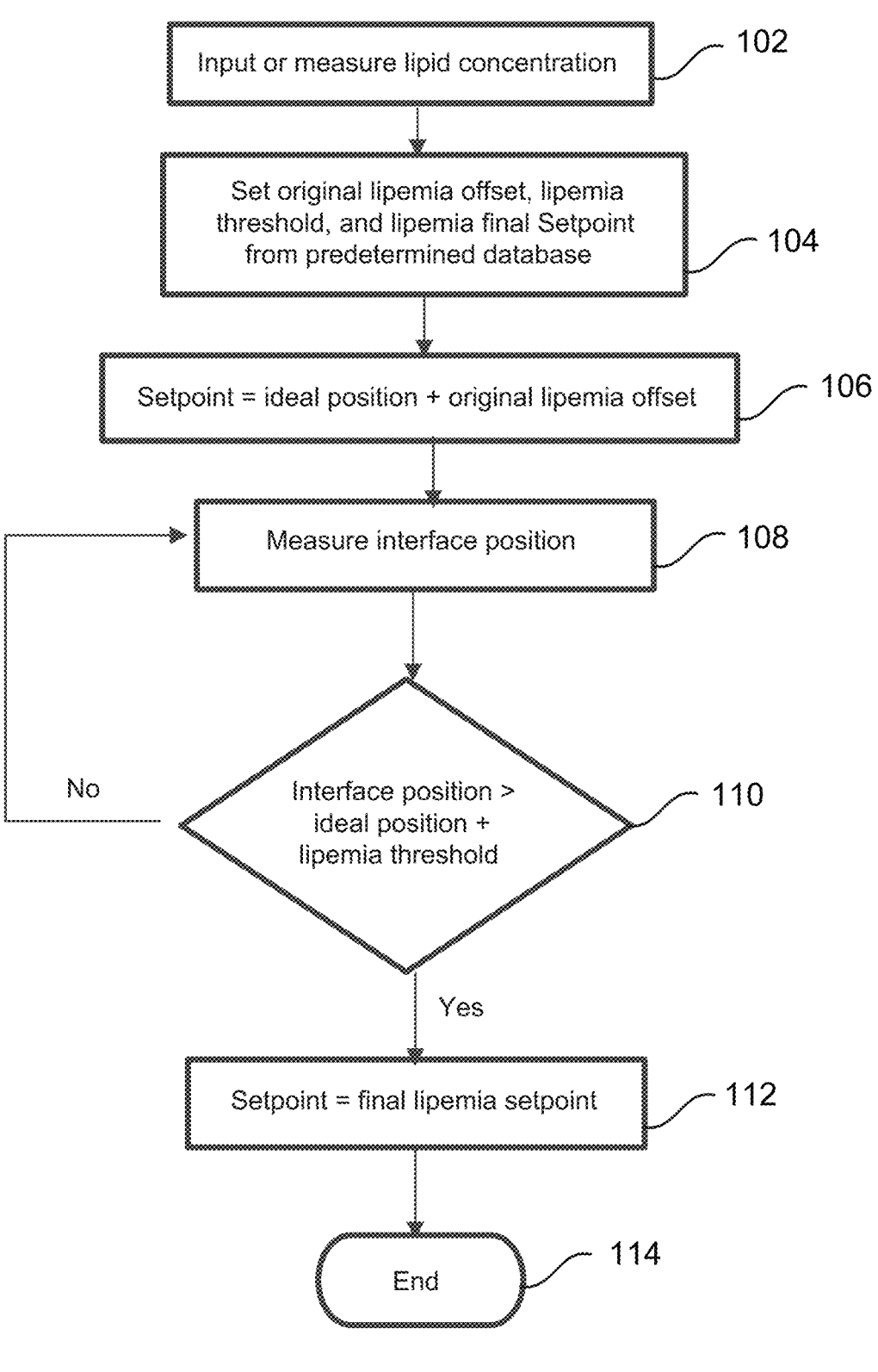
FIG. 19 shows a flow chart of the process utilized with the present disclosure to improve control of the interface position in dealing with lipemia.

As the actual interface begins to increase due to an increase of the plasma flow rate, the artificial interface will likely remain at the same location, or change slightly, since its position is dictated by the decrease of the signal strength due to the lipemic plasma which is not likely to be a strong function of the actual interface position when low, depicted in the progression of the method shown in FIG. 19. As the actual interface position increases, the lipemia offset will begin to decrease but the Error Signal, as measured between the setpoint and artificial interface, will remain constant causing the PID control loop to continue to output a higher plasma rate which will continuously pull the RBC layer 56 higher. As shown in FIG. 18 at D, once the actual interface reaches and surpasses the original ideal position value by a predetermined threshold dependent on the lipemia concentration, the new final setpoint can be adjusted to be set to a higher location than the original ideal position to ensure an artificial interface is not created again later in the procedure. The final lipemia Setpoint will be dependent on the lipid concentrations, with higher concentrations leading to higher final Setpoints. As shown in FIG. 19, the method may repeat throughout a procedure as it is known that lipemia levels may decrease overtime while a collection is in process due to replenishment of lipid-free fluids to the bloodstream to compensate for volumes removed from the body.

Knowing the lipemia offset is important to the method and must be predetermined for varying concentrations of lipids. In order to access a predetermined database of lipemia offset values, the system must accept a known value as a user input 102 or be capable of (preferred) non-invasively measuring the lipemia value present throughout a procedure. This first step 102 of the method shown in FIG. 19 may be accomplished via a second optical based sensor (not shown) attached to the platelet poor plasma, PPP, line of a separator, such as the PPP line exciting the collection side of a separator having a centrifuge pack or the PPP line exiting the spinner of system having a spinning membrane separator.

The second step 104 has the controller set the original lipemia offset, lipemia threshold, and lipemia final Setpoint based on a predetermined database relative to the input or measured lipid concentration. As shown at 106, the Setpoint is equal to the ideal position plus the original lipemia offset. In the next step 108, the system then uses the first optical sensor to measure the interface position. As shown at 110, if the controller determines (No) the interface position is not greater than the ideal position plus the lipemia threshold, then the portion of the process at 108 repeats involving measurement of the interface position and determining whether the interface position is greater than the ideal position plus the lipemia threshold, until (Yes) this is true, at which point 112 the Setpoint established is equal to a final lipemia setpoint. Upon reaching this conclusion, at 114 the method ends.

This new method helps to account for the presence of lipids in the blood to be processed and results in greater efficiency in processing and a higher quality product resulting from the blood separation.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood separation system, comprising:
a blood separation chamber configured to process blood to separate at least one cellular component from plasma;
an input device for providing a lipid concentration within the blood to be processed;
a pump for moving the plasma;
an outlet line associated with the blood separation chamber for removing at least a portion of the plasma from the blood separation chamber;
an optical sensor assembly configured to directly monitor the interior of the blood separation chamber and to measure an interface position between the separated component and the plasma, and to generate an output indicative of the measured interface position;
a predetermined database comprising data providing an original lipemia offset, a lipemia threshold and lipemia final setpoint for varying concentrations of lipids;
a controller programmed to receive the lipid concentration within the blood from the input device and to access the predetermined database to obtain and set the original lipemia offset, the lipemia threshold and lipemia final setpoint based on the value of the concentration of lipids received from the input device, wherein the setpoint equals an ideal interface position that would be required to achieve acceptable separation efficiency of plasma without lipids plus the original lipemia offset, wherein the controller is further programmed with a proportional-integral-derivative control loop to continue to measure the interface position and to assess whether the actual interface position is greater than the ideal interface position plus the lipemia threshold, wherein the controller continues said measuring and assessing until the setpoint equals the lipemia final setpoint; and
wherein the controller is further programmed such that the setpoint is adjusted to be increased to a higher position than the ideal position, wherein the increase is a lipemia offset defined by the difference between a measured artificial higher interface position and an actual interface position.

2. The blood separation system of claim 1, wherein the system further comprises a centrifuge and the blood separation chamber further comprises a centrifugal blood separation chamber configured to be received by the centrifuge.

3. The blood separation system of claim 1, wherein the input device for providing the lipid concentration within the blood to be processed further comprises the controller being programmed to accept a lipid concentration input from an operator input device.

4. The blood separation system of claim 1, wherein the controller is further programmed such that when the setpoint is adjusted by increasing to a higher interface position than the ideal position an error signal is generated that represents the difference between the artificial interface position and the setpoint at the higher interface position.

5. The blood separation system of claim 4, wherein the controller is further programmed to set the flow rate of the plasma pump at which the plasma is removed from the blood separation chamber via an outlet line and such that the error signal causes control logic in the controller to increase the plasma pump flow rate to adjust by increasing the artificial interface position to move toward the increased setpoint, which in turn adjusts by increasing the actual interface position toward the higher ideal interface position.

6. The blood separation system of claim 5, wherein the controller is further programmed such that as the actual interface position begins to increase due to an increase in the plasma flow rate, the artificial interface position remains steady and the lipemia offset begins to decrease but the error signal, as measured between the setpoint and artificial interface position remains constant, wherein the proportional-integral-derivative control loop of the controller will continue to output a higher plasma rate which continues to pull the at least one cellular component layer higher.

7. The blood separation system of claim 6, wherein the controller is further programmed such that once the actual interface position reaches or surpasses the value of the original ideal interface position by a predetermined threshold dependent upon the lipemia concentration, an adjustment is made to a new final interface setpoint that is set to a higher location than the original ideal setpoint position to ensure an artificial interface position is not created again later in the separation procedure.

8. The blood separation system of claim 7, wherein the controller is further programmed to repeat the procedure as lipemia levels decrease overtime while collection is in process due to replenishment of lipid-free fluids to a blood source that compensate for removal of volumes from the blood source.

* * * * *